United States Patent
Pettit et al.

(10) Patent No.: US 12,207,871 B2
(45) Date of Patent: Jan. 28, 2025

(54) REFINING LENS PARAMETERS OF AN OCULAR MODEL

(71) Applicant: Alcon Inc., Fribourg (CH)

(72) Inventors: George Hunter Pettit, Fort Worth, TX (US); Daniil Nekrassov, Berlin (DE); Peter Zieger, Berlin (DE); Martin Gründig, Rangsdorf (DE); Horia Grecu, Berlin (DE); Mark Andrew Zielke, Lake Forest, CA (US); John Alfred Campin, Southlake, TX (US)

(73) Assignee: Alcon Inc., Fribourg (CH)

( * ) Notice: Subject to any disclaimer, the term of this patent is extended or adjusted under 35 U.S.C. 154(b) by 593 days.

(21) Appl. No.: 17/574,667

(22) Filed: Jan. 13, 2022

(65) Prior Publication Data

US 2022/0225869 A1    Jul. 21, 2022

Related U.S. Application Data (60) Provisional application No. 63/139,583, filed on Jan. 20, 2021.

(51) Int. Cl.
*A61B 3/00* (2006.01)
*A61B 3/10* (2006.01)
(Continued)

(52) U.S. Cl.
CPC ............ *A61B 3/0025* (2013.01); *A61B 3/102* (2013.01); *A61B 3/103* (2013.01); *A61B 3/107* (2013.01);
(Continued)

(58) Field of Classification Search
CPC ..... A61B 3/0025; A61B 3/1015; A61B 3/102; A61B 3/103; A61B 3/107; A61B 3/1173;
(Continued)

(56) References Cited

U.S. PATENT DOCUMENTS

| | | |
|---|---|---|
| 2015/0077705 A1 | 3/2015 | Artsyukhovich et al. |
| 2017/0027437 A1 | 2/2017 | Neal et al. |
| 2018/0242840 A1 | 8/2018 | Copland |

FOREIGN PATENT DOCUMENTS

| | | |
|---|---|---|
| WO | 2016089395 A1 | 6/2016 |
| WO | 2017019117 A1 | 2/2017 |

OTHER PUBLICATIONS

Mehdi Bahrami et al, "Geometry-invariant gradient refractive index lens: analytical ray tracing", Journal of Biomedical Optics, May 2012;17:055001.

(Continued)

*Primary Examiner* — Jack Dinh (57) ABSTRACT

An ophthalmic system for generating an ocular model of an eye includes an optical coherence tomography (OCT) device, an aberrometer, and a computer. The OCT device detects OCT light reflected from the eye. The aberrometer detects aberrometer light reflected from the eye. The computer generates the ocular model of the eye according to the reflected OCT light. The ocular model includes parameters describing the eye. The parameters include lens parameters that describe the lens of the eye. The computer determines an OCT-based wavefront according to the ocular model, determines an aberrometer-based wavefront according to the reflected aberrometer light, and compares the OCT-based and the aberrometer-based wavefronts. If the wavefronts differ beyond a predefined tolerance, the computer adjusts one or more values assigned to the parameters until the wavefronts satisfy the predefined tolerance. At least one adjusted value is assigned to a lens parameter.

21 Claims, 6 Drawing Sheets

(51) Int. Cl.
*A61B 3/103* (2006.01)
*A61B 3/107* (2006.01)
*A61B 3/117* (2006.01)
*G06T 15/06* (2011.01)

(52) U.S. Cl.
CPC ............ *A61B 3/1173* (2013.01); *G06T 15/06* (2013.01); *G06T 2210/41* (2013.01)

(58) Field of Classification Search
CPC ........ G16H 40/63; G16H 50/20; G16H 50/30; G16H 50/50; G06T 15/06; G06T 2210/41
See application file for complete search history.

(56) References Cited

OTHER PUBLICATIONS

Navarro et al.,"Adaptive model of the gradient index of the human lens. II. Optics of the accommodating aging lens", Journal of the Optical Society of America A: Optometry, Image Science & Vision, 2007; 24:2911-2920.
Patel et al, "The refractive index of the human cornea: A review", Contact Lens and Anterior Eye 42 (2019) 575-580.
Sheil et al, "Crystalline lens paradoxes revisited: significance of age-related restructuring of the GRIN", Biomedical Optics Express, Sep. 1, 2017; 8:4172-4180.

REFINING LENS PARAMETERS OF AN OCULAR MODEL

TECHNICAL FIELD

The present disclosure relates generally to systems and methods for providing an ocular model of an eye, and more particularly to refining lens parameters of an ocular model.

BACKGROUND

The natural crystalline lens is a complex optic, with two aspheric surfaces and a gradient index of refraction. Adding to the complexity, the gradient index profile may change as the eye ages. In young lenses, the refractive index gradually increases from the surface of the lens to the center. With increasing age, the refractive index distribution becomes more uniform over the central region of the lens, typically forming a plateau, the size of which increases with age. These changes in the refractive index distribution decrease both the optical power of the lens and the contribution of the gradient to the lens power.

Devices that measure the axial dimensions of the eye typically approximate the lens as having a single homogenous refractive index. However, such simplification may lead to errors in calculating eye dimensions. For example, if the net refractive index is higher (or lower) along the optical path through the lens than assumed, then the lens thickness in that region may be calculated as longer (or shorter) than the true value. This in turn may degrade the overall axial length measurement and accuracy of, e.g., IOL power calculations.

BRIEF SUMMARY

In certain embodiments, an ophthalmic system for generating an ocular model of an eye includes an optical coherence tomography (OCT) device, an aberrometer, and a computer. The OCT device directs OCT light towards the eye, and detects the OCT light reflected from the eye. The aberrometer directs aberrometer light towards the eye, and detects the aberrometer light reflected from the eye. The computer generates the ocular model of the eye according to the reflected OCT light. The ocular model includes parameters describing the eye, where each parameter is assigned a value. The parameters include one or more lens parameters that describe a lens of the eye. The computer determines an OCT-based wavefront according to the ocular model, determines an aberrometer-based wavefront according to the reflected aberrometer light, and compares the OCT-based wavefront and the aberrometer-based wavefront. If the OCT-based wavefront and the aberrometer-based wavefront differ beyond a predefined tolerance, the computer adjusts one or more values assigned to one or more parameters of the parameters until the OCT-based wavefront and the aberrometer-based wavefront satisfy the predefined tolerance. At least one adjusted value is assigned to a lens parameter.

Embodiments may include none, one, some, or all of the following features: The lens parameter with the adjusted value describes a refractive index profile of the lens.

The computer adjusts one or more values assigned to one or more parameters by repeating the following until an adjusted OCT-based wavefront and the aberrometer-based wavefront satisfies the predefined tolerance: adjusting the one or more values to yield an adjusted ocular model; determining the adjusted OCT-based wavefront according to the adjusted ocular model; and comparing the adjusted OCT-based wavefront and the aberrometer-based wavefront to see if they satisfy the predefined tolerance.

The computer generates the ocular model of the eye according to the reflected OCT light by applying a ray-tracing procedure.

The computer generates the ocular model of the eye according to the reflected OCT light by: applying a ray-tracing procedure by: defining a plurality of rays traveling through a plurality of anatomical interfaces of the eye; determining locations of the anatomical interfaces according to the rays; and generating the ocular model according to the locations of the anatomical interfaces. The computer may define a ray of the plurality of rays traveling through the anatomical interfaces by repeating the following for each anatomical interface: determining an angle of refraction from an anatomical interface according to a refractive index and an angle of incidence; and determining a distance to the next anatomical interface according to the reflected OCT light.

The system includes a topographer that directs topographer light towards the eye, and detects the topographer light reflected from the eye. The computer may generate the ocular model of the eye by: determining a model-based anterior corneal surface from the ocular model; determining a topographer-based anterior corneal surface from the reflected topographer light; and checking the ocular model by comparing the model-based anterior corneal surface and the topographer-based anterior corneal surface.

The computer generates the ocular model of the eye by checking the ocular model by comparing the ocular model with one or more known measurements of the eye.

The computer determines an OCT-based wavefront according to the ocular model by applying a ray-tracing procedure.

The computer compares the OCT-based wavefront and the aberrometer-based wavefront by: parameterizing the OCT-based wavefront with a plurality of wavefront parameters, each wavefront parameter assigned an OCT-based wavefront value describing the OCT-based wavefront; parameterizing the aberrometer-based wavefront with the plurality of wavefront parameters, each wavefront parameter assigned an aberrometer-based wavefront value describing the aberrometer-based wavefront; and comparing the OCT-based wavefront values and the aberrometer-based wavefront values.

The OCT device checks the ocular model by directing next OCT light towards the eye at an angle different from an angle of the OCT light, and detecting the next OCT light reflected from the eye. The aberrometer checks the ocular model by directing next aberrometer light towards the eye at an angle different from an angle of the aberrometer light, and detecting the next aberrometer light reflected from the eye. The computer checks the ocular model by generating a next ocular model of the eye according to the reflected next OCT light, determining a next OCT-based wavefront according to the next ocular model, and comparing the next OCT-based wavefront and the next aberrometer-based wavefront.

The computer determines a resulting ocular model from the ocular model that yields the OCT-based wavefront that satisfies the predefined tolerance, and plans an ophthalmic surgery according to the resulting ocular model.

The computer determines a resulting ocular model from the ocular model that yields the OCT-based wavefront that satisfies the predefined tolerance, and generates a description of a refractive index profile of the lens according to the resulting ocular model.

In certain embodiments, a method for generating an ocular model of an eye comprises: directing, by an optical coherence tomography (OCT) device, OCT light towards the eye; detecting, by the OCT device, the OCT light reflected from the eye; directing, by an aberrometer, aberrometer light towards the eye; detecting, by the aberrometer, the aberrometer light reflected from the eye; generating, by a computer, the ocular model of the eye according to the reflected OCT light, the ocular model comprising a plurality of parameters describing the eye, each parameter assigned a value, the plurality of parameters comprising one or more lens parameters describing a lens of the eye; determining, by the computer, an OCT-based wavefront according to the ocular model; determining, by the computer, an aberrometer-based wavefront according to the reflected aberrometer light; comparing, by the computer, the OCT-based wavefront and the aberrometer-based wavefront; and if the OCT-based wavefront and the aberrometer-based wavefront differ beyond a predefined tolerance, adjusting, by the computer, one or more values assigned to one or more parameters of the plurality of parameters until the OCT-based wavefront and the aberrometer-based wavefront satisfy the predefined tolerance, at least one adjusted value assigned to a lens parameter of the one or more lens parameters.

Embodiments may include none, one, some, or all of the following features: The method adjusts one or more values assigned to one or more parameters by repeating the following until an adjusted OCT-based wavefront and the aberrometer-based wavefront satisfies the predefined tolerance: adjusting the one or more values to yield an adjusted ocular model; determining the adjusted OCT-based wavefront according to the adjusted ocular model; and comparing the adjusted OCT-based wavefront and the aberrometer-based wavefront to see if they satisfy the predefined tolerance.

The method generates the ocular model of the eye according to the reflected OCT light comprising applying a ray-tracing procedure by: defining a plurality of rays traveling through a plurality of anatomical interfaces of the eye; determining locations of the anatomical interfaces according to the rays; and generating the ocular model according to the locations of the anatomical interfaces.

The method generates the ocular model of the eye by: determining a model-based anterior corneal surface from the ocular model; determining a topographer-based anterior corneal surface from a topographer; and checking the ocular model by comparing the model-based anterior corneal surface and the topographer-based anterior corneal surface.

The method compares the OCT-based wavefront and the aberrometer-based wavefront by: parameterizing the OCT-based wavefront with a plurality of wavefront parameters, each wavefront parameter assigned an OCT-based wavefront value describing the OCT-based wavefront; parameterizing the aberrometer-based wavefront with the plurality of wavefront parameters, each wavefront parameter assigned an aberrometer-based wavefront value describing the aberrometer-based wavefront; and comparing the OCT-based wavefront values and the aberrometer-based wavefront values.

The method further includes directing, by the OCT device, next OCT light towards the eye at an angle different from an angle of the OCT light; detecting, by the OCT device, the next OCT light reflected from the eye; directing, by the aberrometer, next aberrometer light towards the eye at an angle different from an angle of the aberrometer light; detecting, by the aberrometer, the next aberrometer light reflected from the eye; generating, by the computer, a next ocular model of the eye according to the reflected next OCT light; determining, by the computer, a next OCT-based wavefront according to the next ocular model; and comparing, by the computer, the next OCT-based wavefront and the next aberrometer-based wavefront.

In certain embodiments, an ophthalmic system for generating an ocular model of an eye includes an optical coherence tomography (OCT) device, an aberrometer, a topographer, and a computer. The OCT device directs OCT light towards the eye, and detects the OCT light reflected from the eye. The aberrometer directs aberrometer light towards the eye, and detects the aberrometer light reflected from the eye. The topographer directs topographer light towards the eye, and detects the topographer light reflected from the eye. The computer generates the ocular model of the eye according to the reflected OCT light. The ocular model includes parameters describing the eye, where each parameter is assigned a value. The parameters include one or more lens parameters that describe a lens of the eye. The ocular model is generated by applying a ray-tracing procedure by: defining a plurality of rays traveling through a plurality of anatomical interfaces of the eye, a ray of the plurality of rays defined by repeating the following for each anatomical interface: determining an angle of refraction from an anatomical interface according to a refractive index and an angle of incidence, and determining a distance to the next anatomical interface according to the reflected OCT light; determining locations of the anatomical interfaces according to the rays; and generating the ocular model according to the locations of the anatomical interfaces. The ocular model is generated by determining a model-based anterior corneal surface from the ocular model, determining a topographer-based anterior corneal surface from the reflected topographer light, and checking the ocular model by comparing the model-based anterior corneal surface and the topographer-based anterior corneal surface. The ocular model is generated by checking the ocular model by comparing the ocular model with one or more known measurements of the eye. The computer determines an OCT-based wavefront according to the ocular model by applying the ray-tracing procedure, and determines an aberrometer-based wavefront according to the reflected aberrometer light. The computer compares the OCT-based wavefront and the aberrometer-based wavefront. The OCT-based wavefront and the aberrometer-based wavefront are compared by: parameterizing the OCT-based wavefront with a plurality of wavefront parameters, each wavefront parameter assigned an OCT-based wavefront value describing the OCT-based wavefront; parameterizing the aberrometer-based wavefront with the plurality of wavefront parameters, each wavefront parameter assigned an aberrometer-based wavefront value describing the aberrometer-based wavefront; and comparing the OCT-based wavefront values and the aberrometer-based wavefront values. If the OCT-based wavefront and the aberrometer-based wavefront differ beyond a predefined tolerance, the computer adjusts one or more values assigned to one or more parameters of the plurality of parameters until the OCT-based wavefront and the aberrometer-based wavefront satisfy the predefined tolerance. At least one adjusted value is assigned to a lens parameter of the one or more lens parameters, where the lens parameter with the adjusted value describes a refractive index profile of the lens. The one or more values are adjusted by repeating the following until an adjusted OCT-based wavefront and the aberrometer-based wavefront satisfies the predefined tolerance: adjusting the one or more values to yield an adjusted ocular model; determining the adjusted OCT-based wavefront according to the adjusted ocular model; and comparing the adjusted OCT-based wavefront and the aberrometer-based wavefront to see if they satisfy the predefined tolerance. The computer determines a resulting ocular model from the ocular model that yields the OCT-based wavefront that satisfies the predefined tolerance, plans an ophthalmic surgery according to the resulting ocular model, and generates a description of a refractive index profile of the lens according to the resulting ocular model. The OCT device further checks the ocular model by: directing next OCT light towards the eye at an angle different from an angle of the OCT light, and detecting the next OCT light reflected from the eye. The aberrometer further checks the ocular model by: directing next aberrometer light towards the eye at an angle different from an angle of the aberrometer light, and detecting the next aberrometer light reflected from the eye. The computer further checks the ocular model by: generating a next ocular model of the eye according to the reflected next OCT light, determining a next OCT-based wavefront according to the next ocular model, and comparing the next OCT-based wavefront and the next aberrometer-based wavefront.

DESCRIPTION OF EXAMPLE EMBODIMENTS

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

Embodiments of the disclosed systems and methods refine lens parameters of ocular models, such as the refractive index profile of the lens, which may provide advantages. For example, they may yield more accurate dimensional readings, such as axial length and lens thickness. As another example, they may yield more anatomically correct posterior lens topography, which may be useful for sizing accommodative IOLs and for predicting the post-op IOL position. In addition, refined lens parameters may yield information about presbyopia changes in the lens, which may be useful in determining refractive surgery strategies.

Figure 1:
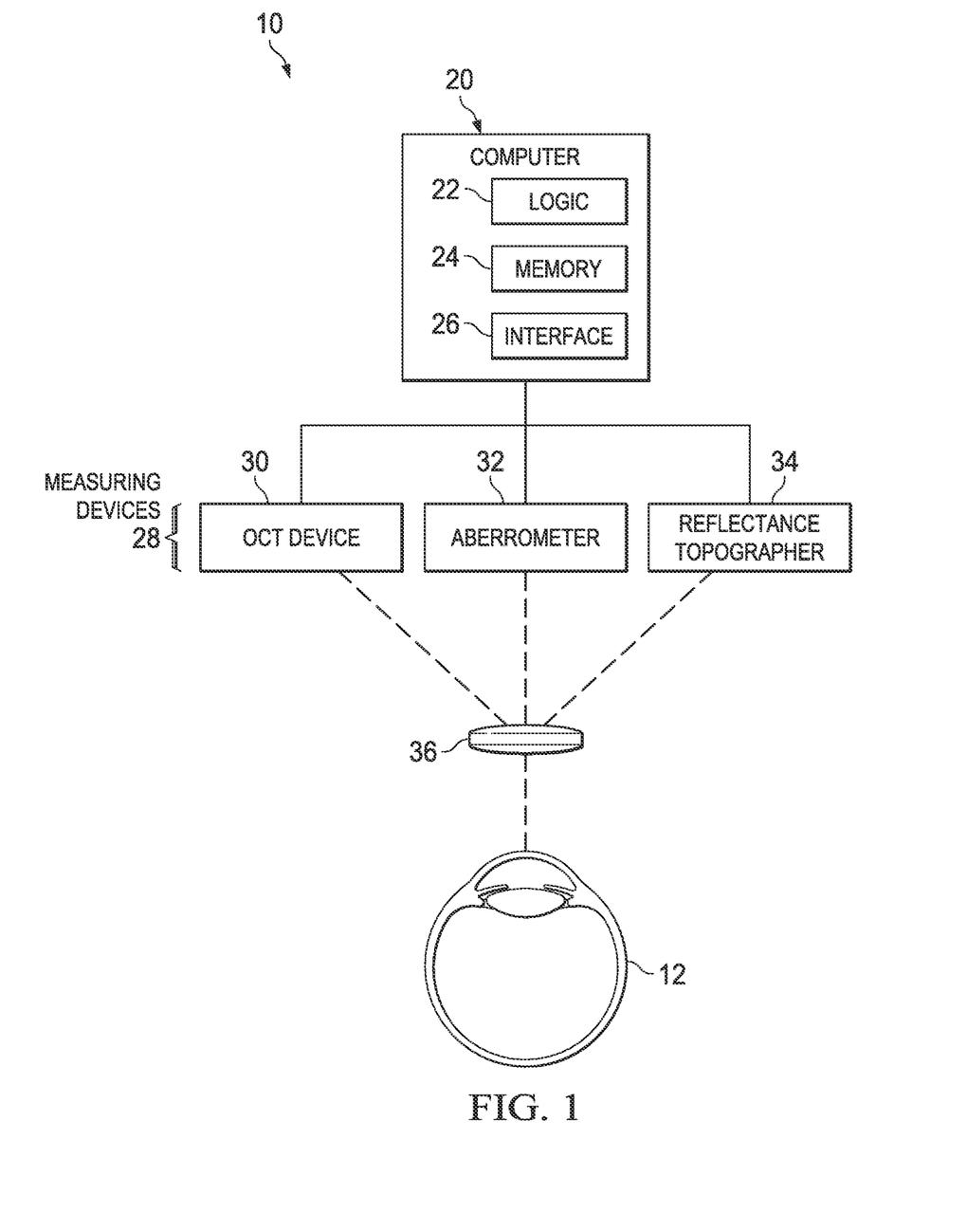
FIG. 1 illustrates an example of a system that provides an ocular model of an eye, according to certain embodiments.

FIG. 1 illustrates an example of a system 10 that provides an ocular model of an eye 12, according to certain embodiments. In the example, system 10 includes a computer 20 (which includes logic 22, a memory 24, and an interface 26), measuring devices 28, and an optical system 36, coupled as shown. Measuring devices 28 include an optical coherence tomography (OCT) device 30, an aberrometer 32, and a topographer 34, coupled as shown.

According to an example of operation, computer 20 generates an ocular model of eye 12 according to measurements from OCT device 30. The ocular model includes lens parameters describing the lens of eye 12. Computer 20 determines an OCT-based wavefront from the ocular model and an aberrometer-based wavefront from aberrometer 32. Computer 20 compares the OCT-based and aberrometer-based wavefronts. If the wavefronts differ beyond a predefined tolerance, computer 20 adjusts at least one value assigned to a lens parameter.

Turning to the parts of system 10, measuring devices 28 include OCT device 30, aberrometer 32, and topographer 34. OCT device 30 directs OCT light towards eye 12 and detects the OCT light reflected from parts of eye 12 to generate an image of the parts. OCT device 30 may be any suitable device that uses OCT to capture two- or three-dimensional images from within optical scattering media, e.g., eye tissue. OCT device 30 may use time domain, frequency domain, or other suitable spectral encoding, and may use single point, parallel, or other suitable scanning. An example of operation is described in more detail with reference to FIG. 2.

Figure 2:
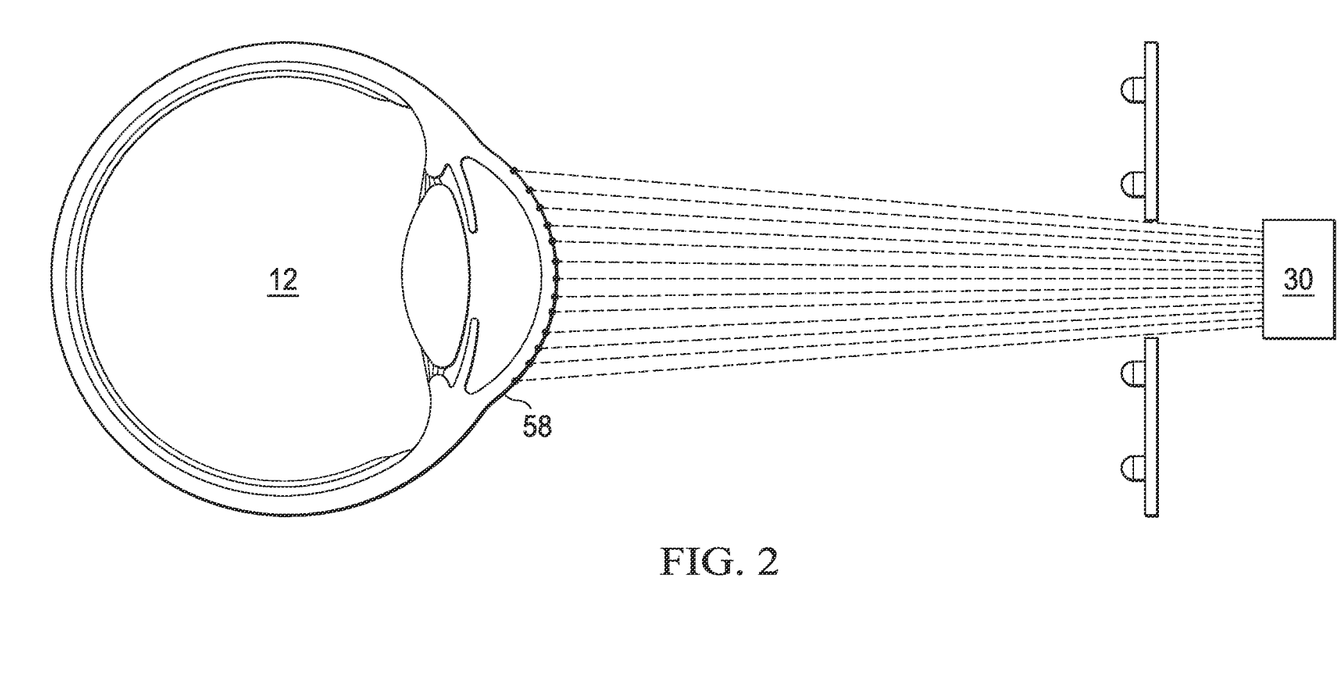
FIG. 2 illustrates an example of an OCT device measuring the anterior corneal surface of an eye.

FIG. 2 illustrates an example of OCT device 30 measuring the anterior corneal surface 58 of eye 12. In general, OCT device 30 detects reflections of light from an interface between media, e.g., between the air and eye 12 or between parts of eye 12, such as between the cornea and aqueous humor. OCT device 30 records the optical path length of the detected light and converts the optical path lengths to physical distances. In certain embodiments, raw data from OCT device 30 is converted such that the distances to the interfaces of eye 12 is expressed "as in air", i.e., not taking into account the refractive indices of the tissue.

In the illustrated example, OCT device 30 detects reflections of light from anterior corneal surface 58, records the optical path length of the detected light, and expresses the distance to anterior corneal surface 58 "as in air". The distances to different points of surface 58 can be used to construct surface 58 in an ocular model. OCT device 30 measures the distances to the interfaces between other parts of eye 12 in a similar manner to construct the rest of the ocular model.

Returning to FIG. 1, aberrometer 32 directs aberrometer light towards eye 12 and detects the aberrometer light reflected from eye 12. Aberrometer 32 uses aberrometry (i.e., wavefront technology) to measure how light travels through eye 12 to retina, which reflects the light. An aberration of the eye causes the light to take on a different shape, which can be used to characterize the aberration. Aberrometer 32 generates a wavefront map (e.g., a Zernike coefficient map) from the reflected light. A Hartmann-Shack aberrometer is an example of an aberrometer 32.

Reflection topographer 34 directs topographer light towards the eye, and detects the topographer light reflected from the eye to measure the shape of anterior corneal surface 58. In certain embodiments, measurements from topographer 34 and OCT device 30 are used to construct anterior corneal surface 58 of the ocular model. An example of operation is described in more detail with reference to FIG. 3.

Figure 3:
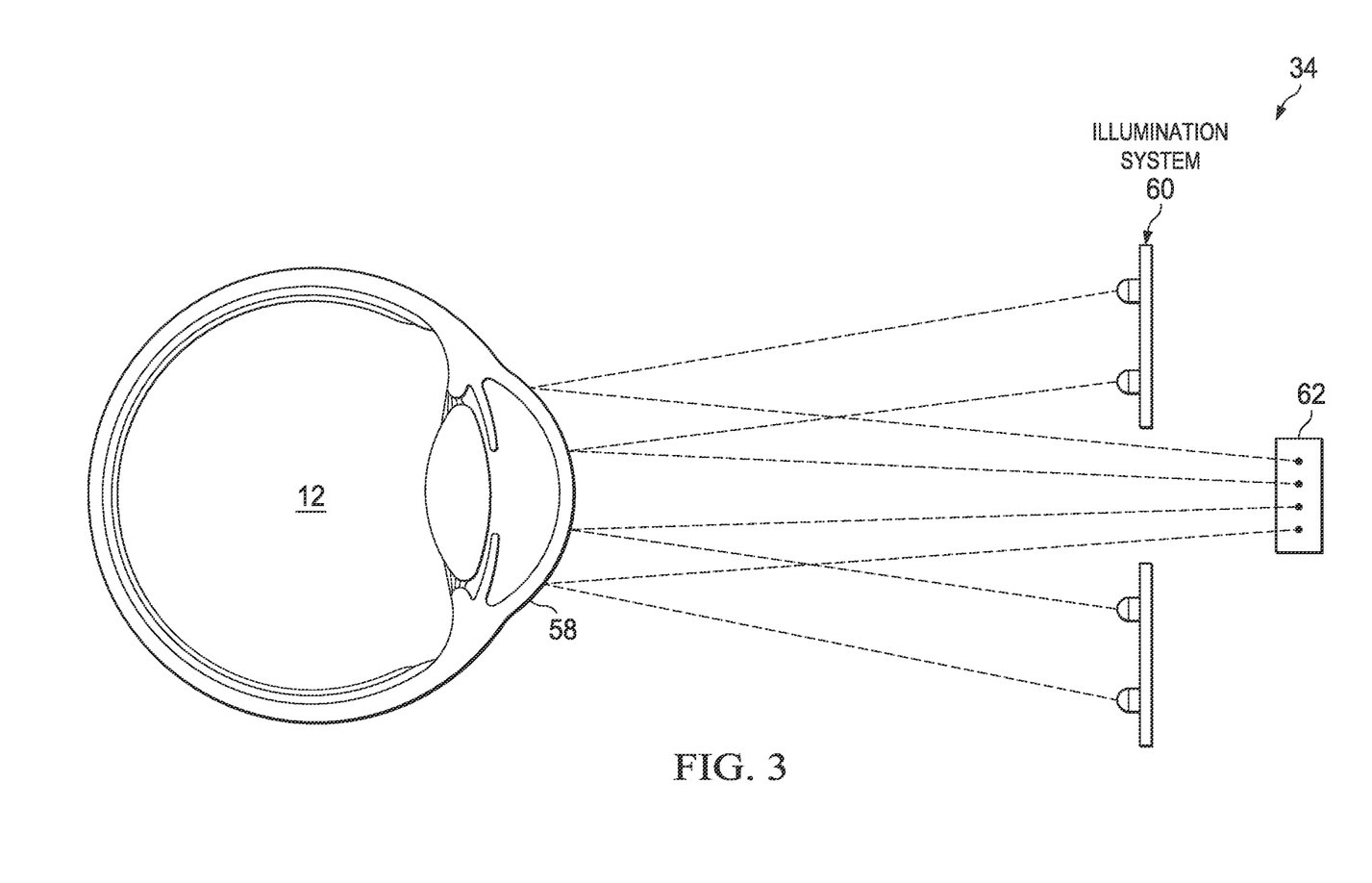
FIG. 3 illustrates an example of a topographer measuring the anterior corneal surface of an eye.

FIG. 3 illustrates an example of a topographer 34, such as a reflection topographer, measuring the anterior corneal surface of eye 12. In the example, topographer 34 includes an illumination system 60 and a sensor 62. Illumination system 60 directs topographer light towards the eye. The light projects a pattern (e.g., concentric rings or grid of dots) onto anterior corneal surface 58. Sensor 62 (e.g., a camera) detects the topographer light reflected from the eye and generates an image of the reflected light. The image is analyzed to determine features of the eye, e.g., the shape of surface 58. If the surface is an ideal sphere, the reflected pattern matches the projected pattern. If the surface has aberrations, areas where the reflected portions of the pattern (e.g. rings or dots) are closer together may indicate steeper corneal curvature, and areas where the portions are farther part may indicate flatter areas. Topographer 34 may output the results in the form of a map of the surface, such as an axial, tangential, refractive power, or elevation map.

Returning to FIG. 1, measuring devices 28 may acquire measurements sequentially and/or simultaneously. To compare the measurements, the measurements should be aligned. In certain cases, the measurements may be aligned using a feature of eye 12, e.g., the pupil or iris markings. In other cases, the measurements may be aligned using eye-tracking functions. In other cases, measuring devices 28 may take measurements along the same optical path such that eye 12 has the same alignment for the measurements. An example of measuring devices 28 making measurements along the same optical path is described with reference to FIG. 4.

Figure 4:
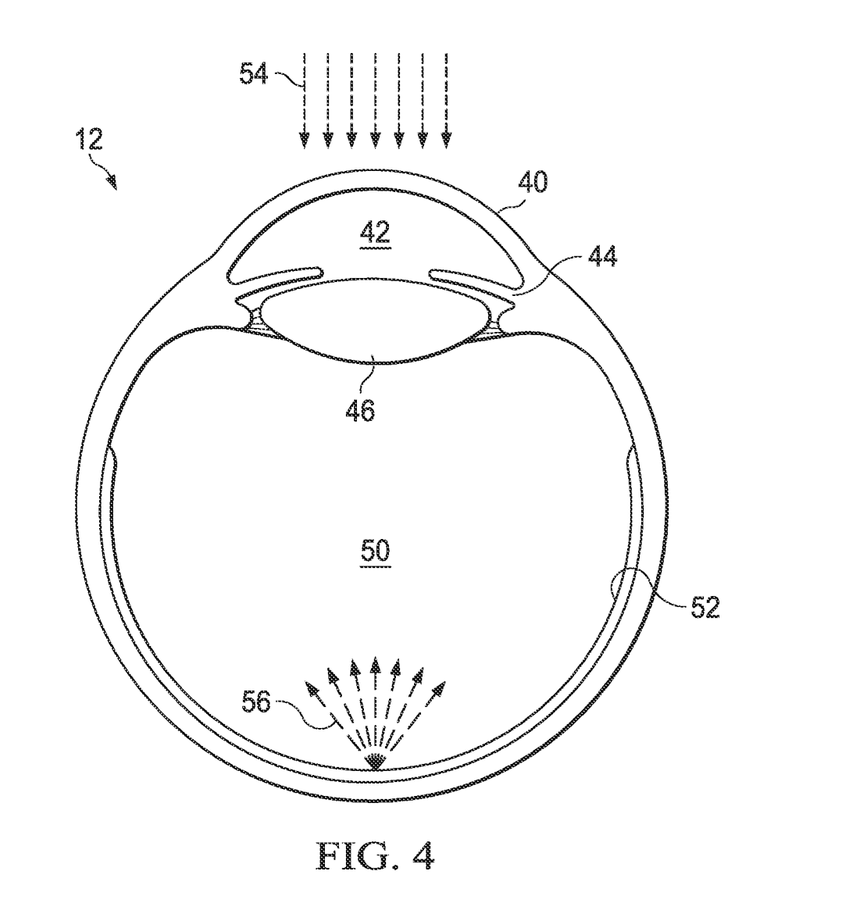
FIG. 4 illustrates an example of OCT light and aberrometer light interacting with an eye.

FIG. 4 illustrates an example of OCT light 54 and aberrometer light 56 interacting with eye 12. In the example, eye 12 includes ocular parts, e.g., a cornea 40, aqueous humor 42, an iris 44, a lens 46, vitreous humor 50, and a retina 52. In certain embodiments, one or more surfaces of and/or the interfaces between parts of eye 12 may be regarded as anatomical interfaces that may be used to generate an ocular model. For example, anatomical interfaces may include: the anterior surface of cornea 40; interfaces between cornea 40, aqueous humor 42, iris 44, lens 46, vitreous humor 50, and/or retina 52; and retina 52.

In the example, OCT beams 54 enter the cornea 40, and aberrometer rays 56 reflect from retina 52. If eye 12 is an ideal emmetrope (with no optical aberrations), then each OCT ray 54 has a reflecting wavefront ray 56 traveling exactly the same optical path, just in reverse. If eye 12 has optical aberrations, the aberrations cause rays 54, 56 from the measurement devices 28 to travel different paths through eye 12. In the illustrated example, OCT beams 54 are parallel. However, OCT beams 54 may have any other suitable beam geometry, e.g., a single scanning OCT beam. As long as the beam geometry is known, the paths of OCT beams 54 can be determined.

Returning to FIG. 1, optical system 36 includes one or more optical elements that direct light from measuring devices 28 towards eye 12. An optical element can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM).

Computer 20 controls the operation of system 10 to refine lens parameters of an ocular model. In certain embodiments, computer 20 generates an ocular model of eye 12 according to measurements from OCT device 30 and then determines an OCT-based wavefront from the ocular model. Computer 20 compares the OCT-based wavefront with an aberrometer-based wavefront from aberrometer 32. If the comparison is not satisfactory, computer 20 adjusts the lens parameter values of the ocular model, and retests the adjusted ocular model by comparing the OCT-based wavefront derived from the adjusted ocular model with the aberrometer-based wavefront until the comparison is satisfactory. In certain embodiments, computer 20 may perform additional checks on the model.

Generating an Ocular Model: Ocular Models. An ocular model may comprise parameters that describe eye 12, where each parameter is assigned a value. A parameter may describe a characteristic (e.g., location, dimension, shape, and/or material property such as refractive index) of a feature (e.g., a part such as the cornea of lens) of eye 12. Parameters may describe, e.g., the following of eye 12 or a part of eye 12: (1) wavefront of eye 12; (2) shape of a surface of a part of eye 12 (e.g., anterior or posterior corneal or lens surface); (3) distance (e.g., physical or optical) through or between parts of eye 12 (e.g., between posterior cornea and anterior lens, between posterior lens and retina, or through cornea, lens, vitreous, or aqueous humor); and refractive index of a part of eye 12. The value assigned to a parameter gives the specific value for the parameter, e.g., the specific thickness of the cornea. As an example, a lens parameter describes features of the lens, e.g., a refractive index profile of the lens. In the example, the refractive index profile may describe the refractive index at particular locations of the lens.

Parameter values are subject to constraints. Constraints can be harder constraints that have a higher priority to be satisfied, or softer constraints with a lower priority to be satisfied. In certain examples, the following parameter values may be certain and be considered harder constraints: (1) whole eye: wavefront; (2) cornea: shape of anterior and posterior surfaces, physical and optical distance through, and refractive index; (3) aqueous humor: physical distance through and refractive index; (4) lens: shape of anterior lens surface, optical path length through, and general refractive index profile (but without specific values); (5) vitreous: physical distance through and refractive index. In the examples, the following parameter values may be uncertain and be considered variables or softer constraints: (1) lens: shape of posterior lens surface, physical path through, and specific values of refractive index profile; (2) vitreous: beam direction through; (3) retina: location, shape of surface.

Generating an Ocular Model: Ray-Tracing. Computer 20 may generate the ocular model according to reflected OCT light in any suitable manner. In certain embodiments, computer 20 applies a ray-tracing procedure to generate the ocular model. Ray-tracing determines the paths of rays through eye 12, including how interfaces between parts of eye 12 refract the ray. At tissue boundaries, refraction is calculated according to according to Snell's Law, which states the ratio of the sines of the angles θ of incidence and refraction is equivalent to the reciprocal of the ratio of the indices of refraction n: $\sin \theta_2 / \sin \theta_1 = n_1/n_2$. A ray traveling through a part of eye 12 with a uniform refractive index propagates in a constant direction, while a ray traveling in a part with a gradient refractive index travels in a curved path. As the rays travel through eye 12, the process calculates the intersections between rays and surfaces, as well as the surface normals at those points, to determine the new direction of the ray according to Snell's Law. The points and surface normals at the points can be used to determine the shape of a surface. An example of such process is described with reference to FIGS. 5A and 5B.

Figure 5A:
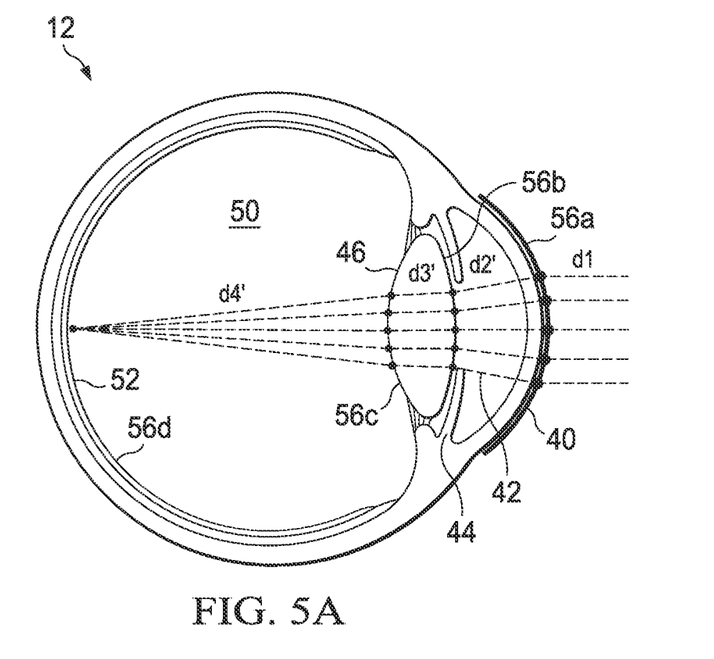
FIGS. 5A and 5B illustrate an example of applying a ray-tracing procedure to determine the locations of the anatomical interfaces of an eye.
Figure 5B:
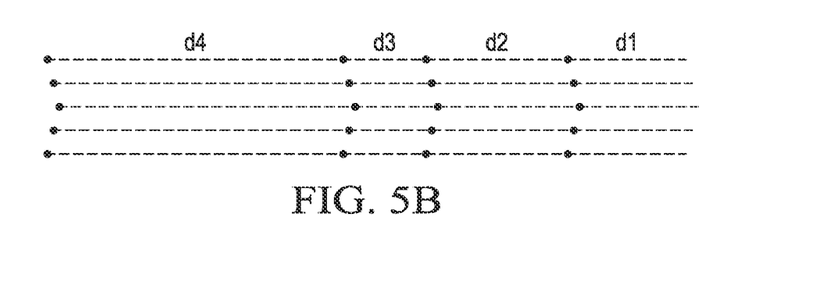

FIGS. 5A and 5B illustrate an example of applying a ray-tracing procedure to determine the locations of the anatomical interfaces 56 of eye 12 in order to generate an ocular model. FIG. 5A illustrates anatomical interfaces 56, which include: interface 56a (anterior corneal surface 58); interface 56b between aqueous humor 42 and lens 46

(anterior lens surface); interface 56c between lens 46 and vitreous humor 50 (posterior lens surface); and interface 56d (surface of retina 52). Distance d' represents the physical distance to an interface 56.

FIG. 5B illustrates measurements from OCT device 30, which records the distances d an OCT ray travels to a point of interfaces 56 as measured "as in air". The ray travels through air to interface 56a, so distance $d_1=d'_1$. However, the ray travels through eye tissue to interfaces 56b to 56d, which decreases the distance, such that $d'_i<d_i$, where i=b, c, and d.

According to an example of operation, computer 20 defines rays traveling through the anatomical interfaces of eye 12, determines the locations of the anatomical interfaces from the rays, and generates the ocular model using the locations of the anatomical interfaces. Computer 20 defines a ray by repeating the following for each anatomical interface: determine the angle of refraction from an anatomical interface using the refractive indices of the tissue and angle of incidence; and determine the distance to the next anatomical interface from the OCT measurements.

In the example, OCT device 30 provides initial "in air" distances d to points of interfaces 56. In certain embodiments, topographer 34 may provide additional measurements for the shape of interface 56a (anterior corneal surface 58). In addition, uncertain parameter values may be assigned initial values that may be adjusted in response to additional information. For example, the refractive index profile of the lens may be initially parameterized, e.g., expressed in terms of parameters with initial values assigned to the parameters. The initial values may be, e.g., average values for a population.

Starting from interface 56a (anterior corneal surface 58), OCT device 30 provides distances $d_1=d'_1$ to points of interface 56a. Distances $d'_2$ to points of interface 56b (anterior lens surface) may be calculated from the distances $d_2$ to the points and the refractive index of the aqueous humor. The angle of refraction at the points of interface 56b may be calculated from the shape of the anterior lens surface, direction of the ray, aqueous humor refractive index, and initial value for the lens refractive index at the points. Distances d' to points of the remaining interfaces 56d and 56d may be calculated in a similar matter.

Computer 20 constructs the ocular model from the lengths and positions of the rays. The points where rays intersect interfaces 56 and surface normals at the points can be used to determine the shape of interfaces 56. In certain embodiments, computer 20 constructs the ocular model by modifying an existing model. In other embodiments, computer 20 constructs the ocular model from the raw data.

In certain cases, computer 20 may take into account additional aspects of eye 12 while generating the eye model. These additional aspects may be found, e.g., in the medical history of eye 12. Examples of such considerations include the refractive index of the IOL of a pseudophakic patient, an atypical corneal refractive index of a previously cross-linked cornea, and an atypical corneal surface of a keratoconic cornea.

Generating an Ocular Model: Checking the Model. In certain embodiments, computer 20 may check the ocular model by comparing one or more parameter values of the ocular model to values of other measurements of eye 12, e.g., measurements from measuring devices 28 of system 10 or external to system 10. A significant deviation among values may indicate a problem. A significant deviation may be, e.g., a deviation outside of one or two standard deviations or greater than a specified percentage such as 2% or 5%. Examples of problems include a problem with: the measurement conditions (e.g., insufficient sampling, inadequate patient fixation, and/or tear film instability), the measuring device 28 (e.g. device alignment and/or calibration), or the parameters of the model (e.g., lens topography parameters). In some cases, a deviation may have a particular signature that indicates the likely problem.

Computer 20 may respond to detecting the deviation in any suitable manner. For example, computer 20 may send a notification identifying one or more related problems, e.g., one or more problems responsible for or likely responsible for the deviation. As another example, computer 20 may provide a recommendation to redo the measurements with one or more measuring devices 28 associated with the deviation, e.g., that could be responsible for the deviation. As another example, computer 20 may identify conditions of eye 12 (e.g., from the medical history of eye 12) that provides context for the deviation and notify the user of the conditions.

Comparing Anterior Corneal Surfaces. In certain embodiments, computer 20 may compare values describing anterior corneal surface 58 of the ocular model with values from other descriptions of anterior corneal surface 58, e.g., measurements of toric power or anterior corneal surface 58 as measured by topographer 34. A significant deviation may indicate a problem with, e.g., insufficient sampling of surface 58 and/or inadequate device issue (e.g., inadequate device alignment or calibration). For example, computer 20 may determine that the measurements of surface 58 from OCT device 30 and/or topographer 34 are insufficient, or that the measurements of OCT device 30 and/or topographer are not aligned with other measurements. Computer 20 may send a notification identifying the problem or likely problems and/or a recommendation to redo the measurements with one or more measuring devices 28 (e.g., OCT device 30 and/or topographer 34) that could be responsible for the deviation.

Determining Wavefronts. Ocular wavefronts are typically measured at the corneal surfaces or entrance pupil plane of the eye. However, the wavefront may be calculated (using aberrometry and/or anatomic OCT data) at any suitable location, e.g., the anterior lens surface. Computer 20 may determine an OCT-based wavefront according to the ocular model in any suitable manner. In certain embodiments, computer 20 determines the OCT-based wavefront by applying a ray-tracing procedure to the ocular model. Rays originating from a spot on the retina are propagated through eye 12, similar to what is shown in FIG. 5A, but in the reverse direction. Computer 20 obtains the position and orientation of the rays at the selected location, and constructs the OCT-based wavefront from the position and orientation. Computer 20 determines the aberrometer-based wavefront according to the reflected aberrometer light from aberrometer 32. In certain embodiments, aberrometer 32 generates a wavefront map, and computer 20 determines the aberrometer-based wavefront from the map.

Comparing Wavefronts. Computer 20 may compare the OCT-based wavefront and the aberrometer-based wavefront in any suitable manner. In certain embodiments, computer compares the wavefronts to see if they differ beyond a predefined tolerance. The predefined tolerance may be defined to accommodate known margins of error of measuring devices 28. For example, the predefined tolerance may be the largest of the known margins of error.

The wavefronts may be parameterized with the same parameters, and computer 20 may compare the wavefronts by comparing the values of the parameters. According to an example of operation, computer 20 parameterizes the OCT-based wavefront with parameters, where each parameter is assigned an OCT-based value that describes the OCT-based wavefront. Computer 20 parameterizes the aberrometer-based wavefront with the parameters, where each parameter is assigned an aberrometer-based value that describes the aberrometer-based wavefront. Computer 20 then compares the OCT-based values with the aberrometer-based values.

Generally, comparing more parameter values may increase the time needed to make the comparison. Accordingly, the number of parameters to compare may be selected in light of expected efficiency. In certain embodiments, computer 20 may perform a faster comparison that compares fewer parameter values in order to identify major deficiencies of the ocular model, which can be addressed before performing a more extensive (yet slower) comparison that compares more parameter values.

According to an example of a fast comparison, computer 20 may check the ocular model by generating a less detailed simulated wavefront. For example, computer 20 may determine a toric representation of interfaces 56 and then calculate sphere and cylinder parameters of a simulated wavefront through interfaces 56. The parameters of the simulated wavefront may be compared to the sphere and cylinder parameters of the aberrometer-based wavefront. A significant deviation may indicate a problem with, e.g., inaccurate axial length measurement, inadequate patient fixation, and/or inadequate device alignment or calibration. Computer 20 may send a notification identifying the problem or likely problems and/or a recommendation to redo the measurements with one or more measuring devices 28 (e.g., OCT device 30 and/or aberrometer 32) that could be responsible for the deviation.

According to another example of a faster comparison, computer 20 may check whether the parameters of the simulated wavefront conform to measurements from, e.g., topographer 34. For example, computer 20 may compare anterior corneal surface 58 of ocular model with surface 58 as measured by topographer 34. In the example, computer 20 determines a model-based anterior corneal surface from the ocular model and a topographer-based anterior corneal surface from topographer 34. Computer 20 checks the ocular model by comparing the model-based and topographer-based anterior corneal surfaces. A significant deviation may indicate a problem with, e.g., the tear film instability and/or inadequate device alignment or calibration. Computer 20 may send a notification identifying the problem or likely problems and/or a recommendation to redo the measurements with one or more measuring devices 28 (e.g., OCT device 30 and/or topographer 34) that could be responsible for the deviation.

According to an example of a more extensive comparison, computer 20 utilizes a wavefront map (e.g., a Zernike coefficient map) that includes wavefront parameters. In the example, computer 20 checks OCT-based values of an OCT-based wavefront with aberrometer-based values of an aberrometer-based wavefront. For example, the slopes of the aberrometer-based wavefront may be compared with the slopes of the rays exiting the eye according to the OCT-based model. Any suitable number of values that reconciles the OCT-based and aberrometer-based values (e.g., slopes) may be checked, e.g., 20 to 50, 50 to 100, or more than 100. The number of values may be adjusted according to desired completeness and/or efficiency. A significant deviation in the higher-order Zernike parametrization may indicate a problem with, e.g., tear film instability, inaccurate lens topography parameters, inadequate patient fixation, and/or inadequate device alignment or calibration. Computer 20 may send a notification identifying the problem or likely problems and/or a recommendation to redo the measurements with one or more measuring devices 28 (e.g., OCT device 30 and/or aberrometer 32) that could be responsible for the deviation.

Adjusting Parameter Values. If the OCT-based wavefront and the aberrometer-based wavefront differ beyond a predefined tolerance, computer 20 adjust one or more parameter values (such as a lens parameter value) of the OCT-based wavefront until a comparison of the wavefronts satisfies the predefined tolerance. Computer 20 adjusts the values by repeating the following: adjust values to yield an adjusted ocular model; determine an adjusted OCT-based wavefront according to the adjusted ocular model; and compare the adjusted OCT-based wavefront and the aberrometer-based wavefront to see if they satisfy the predefined tolerance.

Computer 20 may adjust the parameter values in any suitable manner. In certain embodiments, less certain values are adjusted before more certain values. Less certain values may include values that are not directly measured (e.g., lens refractive indices or cataract grading), values from less reliable measuring devices 28, or values given by softer constraints. More reliable values may include values supported by multiple measurements, values that are generally known in the field, or values given by harder constraints.

Performing Another Check. In certain embodiments, system 10 performs another check of the ocular model. In the embodiments, measuring devices 28 measure eye 12 from a different angle than was previously used to measure eye 12, and the measurements are compared. For example, measuring device 28 may first measure eye "on-axis", i.e., the optical axis of measuring device 28 is aligned with an axis (e.g., visual or optical) of eye 12. To check the ocular model, measuring device 28 may measure eye "off-axis", i.e., the axis of measuring device 28 is at an angle with the axis of eye. The angle may be, e.g., 0 to 10, and/or 10 to 20 degrees, such as approximately 3 degrees. Computer 20 uses the measurements at the different angle to generate new wavefronts to compare in order to check the ocular model.

For example, OCT device 30 directs OCT light towards the eye at the different angle and detects the OCT light reflected from the eye. Aberrometer 32 directs aberrometer light towards the eye at the different angle, detects the aberrometer light reflected from the eye, and generates an aberrometer-based wavefront. Computer 20 generates another ocular model of the eye according to the reflected OCT light and determines an OCT-based wavefront from the ocular model. Computer 20 then compares the wavefronts to check the ocular model.

Computer 20 stores the resulting ocular model in memory 24 and may output the model via interface 26. In certain embodiments, computer 20 uses the resulting ocular model to plan an ophthalmic surgery, e.g., a cataract or refractive surgery. For example, the model may be used to size accommodative intraocular lenses (IOLs) or to predict the post-operation position of an IOL. In other embodiments, computer 20 generates a refractive index profile of the lens from the resulting ocular model. The profile may be used to, e.g., detect presbyopia changes in the lens, which may be used to determine a refractive surgery strategy.

Figure 6:
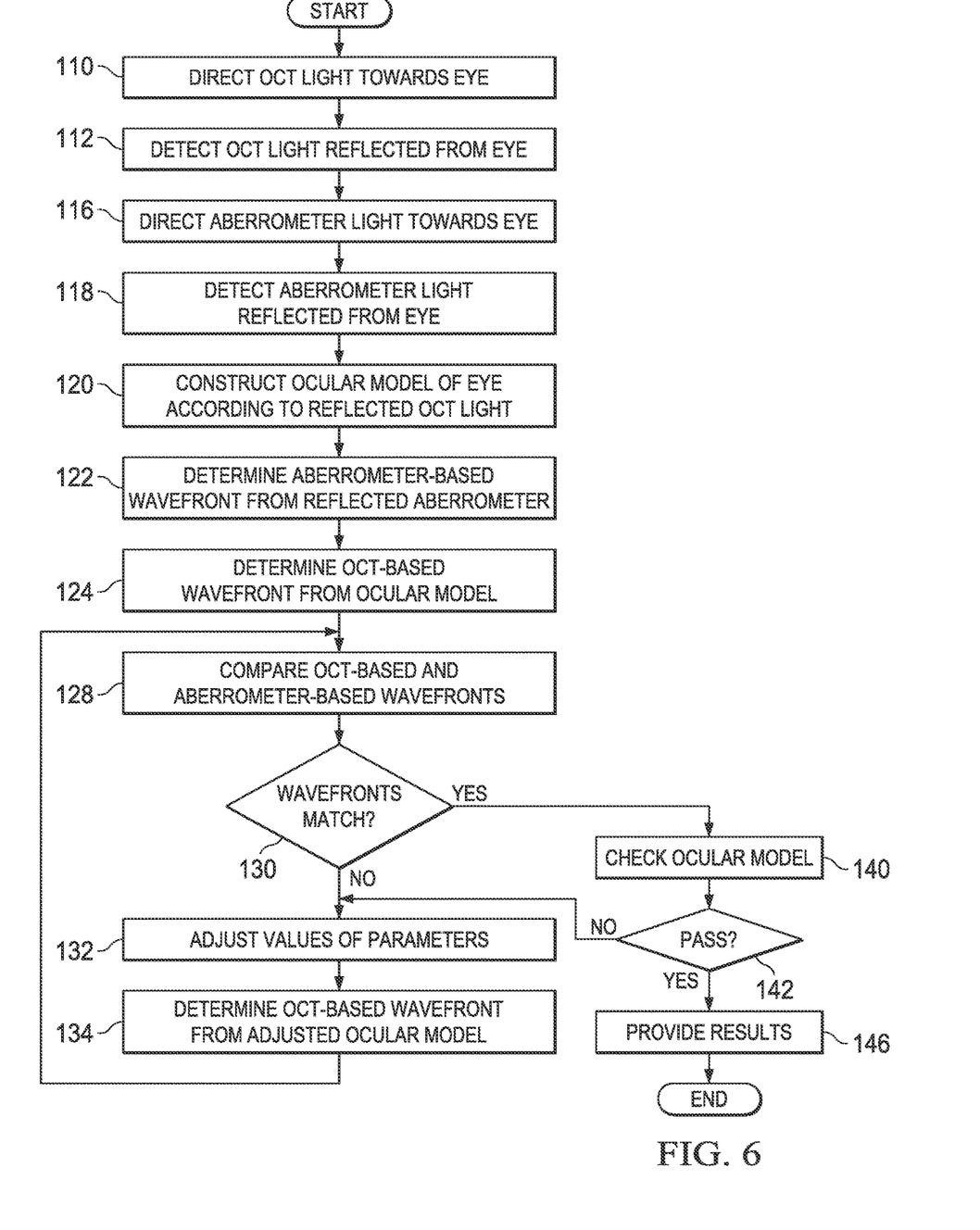
FIG. 6 illustrates an example of a method for generating an eye model that may be performed by the system of FIG. 1, according to certain embodiments.

FIG. 6 illustrates an example of a method for generating an eye model that may be performed by system 10 of FIG. 1, according to certain embodiments. In certain embodiments, computer 20 may perform steps of the method by sending instructions to the components of system 10.

The method starts at step 110, where OCT device 30 directs a beam of OCT light towards the tissue of an eye, which reflects the light. OCT device 30 detects the reflected OCT light at step 112. Aberrometer 32 directs a beam of aberrometer light towards the tissue at step 114, and detects the aberrometer light reflected from the tissue at step 116.

Computer 20 generates an ocular model of the eye according to the reflected OCT light at step 120. In certain embodiments, computer 20 applies a ray-tracing procedure to generate the ocular model by: defining rays traveling through anatomical interfaces of the eye; determining the locations of the anatomical interfaces according to the rays; and generating the ocular model according to the locations of the anatomical interfaces. A ray traveling through the anatomical interfaces may be defined by repeating the following for each anatomical interface: determining an angle of refraction from an anatomical interface according to a refractive index and an angle of incidence; and determining a distance to the next anatomical interface according to the reflected OCT light.

Certain embodiments may include variations in generating the ocular model. For example, computer 20 may construct the anterior corneal surface of the ocular model according to measurements from OCT device 30 and topographer 34. As another example, computer 20 may check the ocular model by comparing the ocular model with other measurements of the eye, e.g., toric measurements.

Computer 20 determines an OCT-based wavefront according to the ocular model at step 122. Computer 20 may apply a ray-tracing process to calculate the OCT-based wavefront. Computer 20 determines an aberrometer-based wavefront according to the reflected aberrometer light at step 124. In certain embodiments, aberrometer 32 generates a wavefront map and provides the map to computer 20.

Computer 20 compares the OCT-based and aberrometer-based wavefronts at step 128. Computer 20 may compare the wavefronts by: parameterizing the OCT-based wavefront with wavefront parameters, each parameter assigned an OCT-based wavefront value describing the OCT-based wavefront; parameterizing the aberrometer-based wavefront with the wavefront parameters, each parameter assigned an aberrometer-based wavefront value describing the aberrometer-based wavefront; and comparing the OCT-based wavefront values and the aberrometer-based wavefront values.

The wavefronts may match at step 130 within a predefined tolerance. If the wavefronts do not match at step 130, computer 20 adjusts one or more parameter values at step 132 to yield an adjusted ocular model. The method then proceeds to step 134 to determine an OCT-based wavefront from the adjusted ocular model. The method then returns to step 128 to compare the adjusted OCT-based wavefront with the aberrometer-based wavefront.

If the wavefronts match at step 130, the method proceeds to step 140, where computer 20 checks the ocular model. To check the model, measuring devices 30 (e.g., OCT device 30 and aberrometer 32) measure eye 12 from a different angle. Computer 20 generates next wavefronts from the new measurements to compare to check the ocular model.

The ocular model may pass the check at step 142. If the ocular model passes, the method proceeds to step 146, where computer 20 provides the results. Computer 20 may display the results and/or use the results in any suitable manner. For example, the results may be used to plan an ophthalmic surgery (e.g., cataract or refractive) or to generate a description of the refractive index profile of the lens. The method then ends.

A component (such as computer 20) of the systems and apparatuses disclosed herein may include an interface, logic, and/or memory, any of which may include computer hardware and/or software. An interface can receive input to the component and/or send output from the component, and is typically used to exchange information between, e.g., software, hardware, a peripheral device, a user, and/or other external entity. A user may use an interface, such as a Graphical User Interface (GUI) or an interface device, to interact with (e.g., provide input and/or receive output) a computer. Examples of interface devices include input and/or output devices, such as a keyboard, mouse, touchpad, touchscreen, microphone, display, foot pedal, gesture sensor, and/or speaker.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by the electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic system for generating an ocular model of an eye, the system comprising:
   an optical coherence tomography (OCT) device configured to:
      direct OCT light towards the eye; and
      detect the OCT light reflected from the eye;
   an aberrometer configured to:
      direct aberrometer light towards the eye; and
      detect the aberrometer light reflected from the eye; and
   a computer configured to:
      generate the ocular model of the eye according to the reflected OCT light, the ocular model comprising a plurality of parameters describing the eye, each parameter assigned a value, the plurality of parameters comprising one or more lens parameters describing a lens of the eye;
      determine an OCT-based wavefront according to the ocular model;
      determine an aberrometer-based wavefront according to the reflected aberrometer light;
      compare the OCT-based wavefront and the aberrometer-based wavefront; and
      if the OCT-based wavefront and the aberrometer-based wavefront differ beyond a predefined tolerance, adjust one or more values assigned to one or more parameters of the plurality of parameters until the OCT-based wavefront and the aberrometer-based wavefront satisfy the predefined tolerance, at least one adjusted value assigned to a lens parameter of the one or more lens parameters.

2. The ophthalmic system of claim 1, wherein the lens parameter with the adjusted value describes a refractive index profile of the lens.

3. The ophthalmic system of claim 1, wherein the computer is configured to adjust one or more values assigned to one or more parameters by:
   repeating the following until an adjusted OCT-based wavefront and the aberrometer-based wavefront satisfies the predefined tolerance:
      adjusting the one or more values to yield an adjusted ocular model;
      determining the adjusted OCT-based wavefront according to the adjusted ocular model; and
      comparing the adjusted OCT-based wavefront and the aberrometer-based wavefront to see if they satisfy the predefined tolerance.

4. The ophthalmic system of claim 1, wherein the computer is configured to generate the ocular model of the eye according to the reflected OCT light by:
   applying a ray-tracing procedure.

5. The ophthalmic system of claim 1, wherein the computer is configured to generate the ocular model of the eye according to the reflected OCT light by:
   applying a ray-tracing procedure by:
      defining a plurality of rays traveling through a plurality of anatomical interfaces of the eye;
      determining locations of the anatomical interfaces according to the rays; and
      generating the ocular model according to the locations of the anatomical interfaces.

6. The ophthalmic system of claim 5, wherein the computer is configured to define a ray of the plurality of rays traveling through the anatomical interfaces by:
   repeating the following for each anatomical interface:
      determining an angle of refraction from an anatomical interface according to a refractive index and an angle of incidence; and
      determining a distance to the next anatomical interface according to the reflected OCT light.

7. The ophthalmic system of claim 1, further comprising a topographer configured to:
   direct topographer light towards the eye; and
   detect the topographer light reflected from the eye.

8. The ophthalmic system of claim 7, the computer configured to generate the ocular model of the eye by:
   determining a model-based anterior corneal surface from the ocular model;
   determining a topographer-based anterior corneal surface from the reflected topographer light; and
   checking the ocular model by comparing the model-based anterior corneal surface and the topographer-based anterior corneal surface.

9. The ophthalmic system of claim 1, the computer configured to generate the ocular model of the eye by:
   checking the ocular model by comparing the ocular model with one or more known measurements of the eye.

10. The ophthalmic system of claim 1, the computer configured to determine an OCT-based wavefront according to the ocular model by:
    applying a ray-tracing procedure.

11. The ophthalmic system of claim 1, the computer configured to compare the OCT-based wavefront and the aberrometer-based wavefront by:
    parameterizing the OCT-based wavefront with a plurality of wavefront parameters, each wavefront parameter assigned an OCT-based wavefront value describing the OCT-based wavefront;
    parameterizing the aberrometer-based wavefront with the plurality of wavefront parameters, each wavefront parameter assigned an aberrometer-based wavefront value describing the aberrometer-based wavefront; and
    comparing the OCT-based wavefront values and the aberrometer-based wavefront values.

12. The ophthalmic system of claim 1:
    the OCT device further configured to check the ocular model by:
       directing next OCT light towards the eye at an angle different from an angle of the OCT light; and
       detecting the next OCT light reflected from the eye; and
    the aberrometer further configured to check the ocular model by:
       directing next aberrometer light towards the eye at an angle different from an angle of the aberrometer light; and
       detecting the next aberrometer light reflected from the eye; and
    the computer further configured to check the ocular model by:
       generating a next ocular model of the eye according to the reflected next OCT light;
       determining a next OCT-based wavefront according to the next ocular model; and
       comparing the next OCT-based wavefront and the next aberrometer-based wavefront.

13. The ophthalmic system of claim 1, the computer further configured to:
    determine a resulting ocular model from the ocular model that yields the OCT-based wavefront that satisfies the predefined tolerance; and
    plan an ophthalmic surgery according to the resulting ocular model.

14. The ophthalmic system of claim 1, the computer further configured to:
   determine a resulting ocular model from the ocular model that yields the OCT-based wavefront that satisfies the predefined tolerance; and
   generate a description of a refractive index profile of the lens according to the resulting ocular model.

15. A method for generating an ocular model of an eye, comprising:
   directing, by an optical coherence tomography (OCT) device, OCT light towards the eye;
   detecting, by the OCT device, the OCT light reflected from the eye;
   directing, by an aberrometer, aberrometer light towards the eye;
   detecting, by the aberrometer, the aberrometer light reflected from the eye;
   generating, by a computer, the ocular model of the eye according to the reflected OCT light, the ocular model comprising a plurality of parameters describing the eye, each parameter assigned a value, the plurality of parameters comprising one or more lens parameters describing a lens of the eye;
   determining, by the computer, an OCT-based wavefront according to the ocular model;
   determining, by the computer, an aberrometer-based wavefront according to the reflected aberrometer light;
   comparing, by the computer, the OCT-based wavefront and the aberrometer-based wavefront; and
   if the OCT-based wavefront and the aberrometer-based wavefront differ beyond a predefined tolerance, adjusting, by the computer, one or more values assigned to one or more parameters of the plurality of parameters until the OCT-based wavefront and the aberrometer-based wavefront satisfy the predefined tolerance, at least one adjusted value assigned to a lens parameter of the one or more lens parameters.

16. The method of claim 15, the adjusting one or more values assigned to one or more parameters comprising:
   repeating the following until an adjusted OCT-based wavefront and the aberrometer-based wavefront satisfies the predefined tolerance:
      adjusting the one or more values to yield an adjusted ocular model;
      determining the adjusted OCT-based wavefront according to the adjusted ocular model; and
      comparing the adjusted OCT-based wavefront and the aberrometer-based wavefront to see if they satisfy the predefined tolerance.

17. The method of claim 15, the generating the ocular model of the eye according to the reflected OCT light comprising applying a ray-tracing procedure by:
   defining a plurality of rays traveling through a plurality of anatomical interfaces of the eye;
   determining locations of the anatomical interfaces according to the rays; and
   generating the ocular model according to the locations of the anatomical interfaces.

18. The method of claim 15, the generating the ocular model of the eye comprising:
   determining a model-based anterior corneal surface from the ocular model; and
   determining a topographer-based anterior corneal surface from a topographer; and
   checking the ocular model by comparing the model-based anterior corneal surface and the topographer-based anterior corneal surface.

19. The method of claim 15, the comparing the OCT-based wavefront and the aberrometer-based wavefront comprising:
   parameterizing the OCT-based wavefront with a plurality of wavefront parameters, each wavefront parameter assigned an OCT-based wavefront value describing the OCT-based wavefront;
   parameterizing the aberrometer-based wavefront with the plurality of wavefront parameters, each wavefront parameter assigned an aberrometer-based wavefront value describing the aberrometer-based wavefront; and
   comparing the OCT-based wavefront values and the aberrometer-based wavefront values.

20. The method of claim 15, further comprising:
   directing, by the OCT device, next OCT light towards the eye at an angle different from an angle of the OCT light;
   detecting, by the OCT device, the next OCT light reflected from the eye;
   directing, by the aberrometer, next aberrometer light towards the eye at an angle different from an angle of the aberrometer light;
   detecting, by the aberrometer, the next aberrometer light reflected from the eye;
   generating, by the computer, a next ocular model of the eye according to the reflected next OCT light;
   determining, by the computer, a next OCT-based wavefront according to the next ocular model; and
   comparing, by the computer, the next OCT-based wavefront and the next aberrometer-based wavefront.

21. An ophthalmic system for generating an ocular model of an eye, the system comprising:
   an optical coherence tomography (OCT) device configured to:
      direct OCT light towards the eye; and
      detect the OCT light reflected from the eye;
   an aberrometer configured to:
      direct aberrometer light towards the eye; and
      detect the aberrometer light reflected from the eye;
   a topographer configured to:
      direct topographer light towards the eye; and
      detect the topographer light reflected from the eye; and
   a computer configured to:
      generate the ocular model of the eye according to the reflected OCT light, the ocular model comprising a plurality of parameters describing the eye, each parameter assigned a value, the plurality of parameters comprising one or more lens parameters describing a lens of the eye, the ocular model generated by:
         applying a ray-tracing procedure by: defining a plurality of rays traveling through a plurality of anatomical interfaces of the eye, a ray of the plurality of rays defined by repeating the following for each anatomical interface: determining an angle of refraction from an anatomical interface according to a refractive index and an angle of incidence, and determining a distance to the next anatomical interface according to the reflected OCT light; determining locations of the anatomical interfaces according to the rays; and generating the ocular model according to the locations of the anatomical interfaces;
         determining a model-based anterior corneal surface from the ocular model, determining a topographer-based anterior corneal surface from the reflected topographer light, and checking the ocular model by comparing the model-based anterior corneal surface and the topographer-based anterior corneal surface; and
checking the ocular model by comparing the ocular model with one or more known measurements of the eye;
determine an OCT-based wavefront according to the ocular model by applying the ray-tracing procedure;
determine an aberrometer-based wavefront according to the reflected aberrometer light;
compare the OCT-based wavefront and the aberrometer-based wavefront, the OCT-based wavefront and the aberrometer-based wavefront compared by: parameterizing the OCT-based wavefront with a plurality of wavefront parameters, each wavefront parameter assigned an OCT-based wavefront value describing the OCT-based wavefront; parameterizing the aberrometer-based wavefront with the plurality of wavefront parameters, each wavefront parameter assigned an aberrometer-based wavefront value describing the aberrometer-based wavefront; and comparing the OCT-based wavefront values and the aberrometer-based wavefront values;
if the OCT-based wavefront and the aberrometer-based wavefront differ beyond a predefined tolerance, adjust one or more values assigned to one or more parameters of the plurality of parameters until the OCT-based wavefront and the aberrometer-based wavefront satisfy the predefined tolerance, at least one adjusted value assigned to a lens parameter of the one or more lens parameters, the lens parameter with the adjusted value describing a refractive index profile of the lens, the one or more values assigned to one or more parameters adjusted by repeating the following until an adjusted OCT-based wavefront and the aberrometer-based wavefront satisfies the predefined tolerance:
adjusting the one or more values to yield an adjusted ocular model;
determining the adjusted OCT-based wavefront according to the adjusted ocular model; and
comparing the adjusted OCT-based wavefront and the aberrometer-based wavefront to see if they satisfy the predefined tolerance;
determine a resulting ocular model from the ocular model that yields the OCT-based wavefront that satisfies the predefined tolerance;
plan an ophthalmic surgery according to the resulting ocular model; and
generate a description of a refractive index profile of the lens according to the resulting ocular model;
the OCT device further configured to check the ocular model by:
directing next OCT light towards the eye at an angle different from an angle of the OCT light; and
detecting the next OCT light reflected from the eye; and
the aberrometer further configured to check the ocular model by:
directing next aberrometer light towards the eye at an angle different from an angle of the aberrometer light; and
detecting the next aberrometer light reflected from the eye; and
the computer further configured to check the ocular model by:
generating a next ocular model of the eye according to the reflected next OCT light;
determining a next OCT-based wavefront according to the next ocular model; and
comparing the next OCT-based wavefront and the next aberrometer-based wavefront.

* * * * *